US00PP32972P2

(12) United States Plant Patent
Oprins

(10) Patent No.: US PP32,972 P2
(45) Date of Patent: Apr. 13, 2021

(54) ***HYDRANGEA* PLANT NAMED 'HPOPR018'**

(50) Latin Name: *Hydrangea paniculata*
Varietal Denomination: HPOPR018

(71) Applicant: OPRINS PLANT N.V., Rijkevorsel (BE)

(72) Inventor: Jan Oprins, Rijkevorsel (BE)

(73) Assignee: OPRINS PLANT N.V., Rijkevorsel (BE)

( * ) Notice: Subject to any disclaimer, the term of this patent is extended or adjusted under 35 U.S.C. 154(b) by 0 days.

(21) Appl. No.: 16/873,312

(22) Filed: Mar. 18, 2020

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — Penny J Aguirre

(57) ABSTRACT

A new cultivar of *Hydrangea paniculata* plant named 'HPOPR018' that is characterized by its compact plant habit, its early blooming season, and its compact panicles of primarily white sterile and fertile flowers with the fertile flowers clearly visible.

2 Drawing Sheets

CROSS-REFERENCE TO A RELATED APPLICATION

This application is related to a European plant breeders' rights application filed on Oct. 24, 2017, application No. 2017/2687. There have been no offers for sale anywhere in the world prior to the effective filing date of this Application and no accessibility to one of ordinary skill in the art could have been derived from the printed plant breeder's rights documents.

Botanical classification: *Hydrangea paniculata.*
Varietal denomination: 'HPOPR018'.

BACKGROUND OF THE INVENTION

The present invention relates to a new and distinct cultivar of *Hydrangea paniculata* and will be referred to hereafter by its cultivar name, 'HPOPR018'. 'HPOPR018' represents a new *Hydrangea*, a perennial shrub grown for landscape use and as a potted plant.

'HPOPR018' was derived from a breeding program conducted by the Inventor at a nursery in Merksplas, Belgium. The objective of the breeding program is to select new cultivars of *Hydrangea* with a compact plant habit and desirable flowers.

'HPOPR018' was selected in August of 2015 by the Inventor from amongst seedlings in a trial field that had been planted with seed collected from open pollination of numerous plants in the Inventor's breeding program in August of 2012. The exact parentage is therefore unknown.

Asexual propagation of the new cultivar was first accomplished by softwood stem cuttings by the Inventor in September of 2015 in Merksplas, Belgium. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'HPOPR018' as a unique cultivar of *Hydrangea.*

1. 'HPOPR018' exhibits a compact plant habit.
2. 'HPOPR018' exhibits an early blooming season.
3. 'HPOPR018' exhibits compact panicles of primarily white sterile and fertile flowers with the fertile flowers clearly visible.

'HPOPR018' can be most closely compared to the *Hydrangea paniculata* cultivars 'Wim's Red' (U.S. Plant Pat. No. 26,005) and 'Bulk' (U.S. Plant Pat. No. 16,812), 'Wim's Red' is similar to 'HPOPR018' in having a compact plant habit and inflorescences with sterile and fertile flowers with fertile flowers being clearly visible. 'Wim's Red' differs from 'HPOPR018' in having a slightly taller plant height, a coarser plant structure, flowers that open later in the season and sterile flowers that change to red in color later in the season. 'Bulk' is similar to 'HPOPR018' in having a compact plant habit. 'Bulk' differs from 'HPOPR018' in having inflorescences that are more open and stretched in shape and sterile flowers that change to deep reddish pink in color.

BRIEF DESCRIPTION OF THE DRAWINGS

The accompanying colored photographs illustrate the overall appearance and distinct characteristics of the new *Hydrangea*. The photographs were taken of a two-year-old plant of 'HPOPR018' as grown outdoors in a 17-cm container in Boskoop, The Netherlands.

The photograph in FIG. 1 provides a side view of the plant habit of 'HPOPR018' in bloom.

Figure 1:
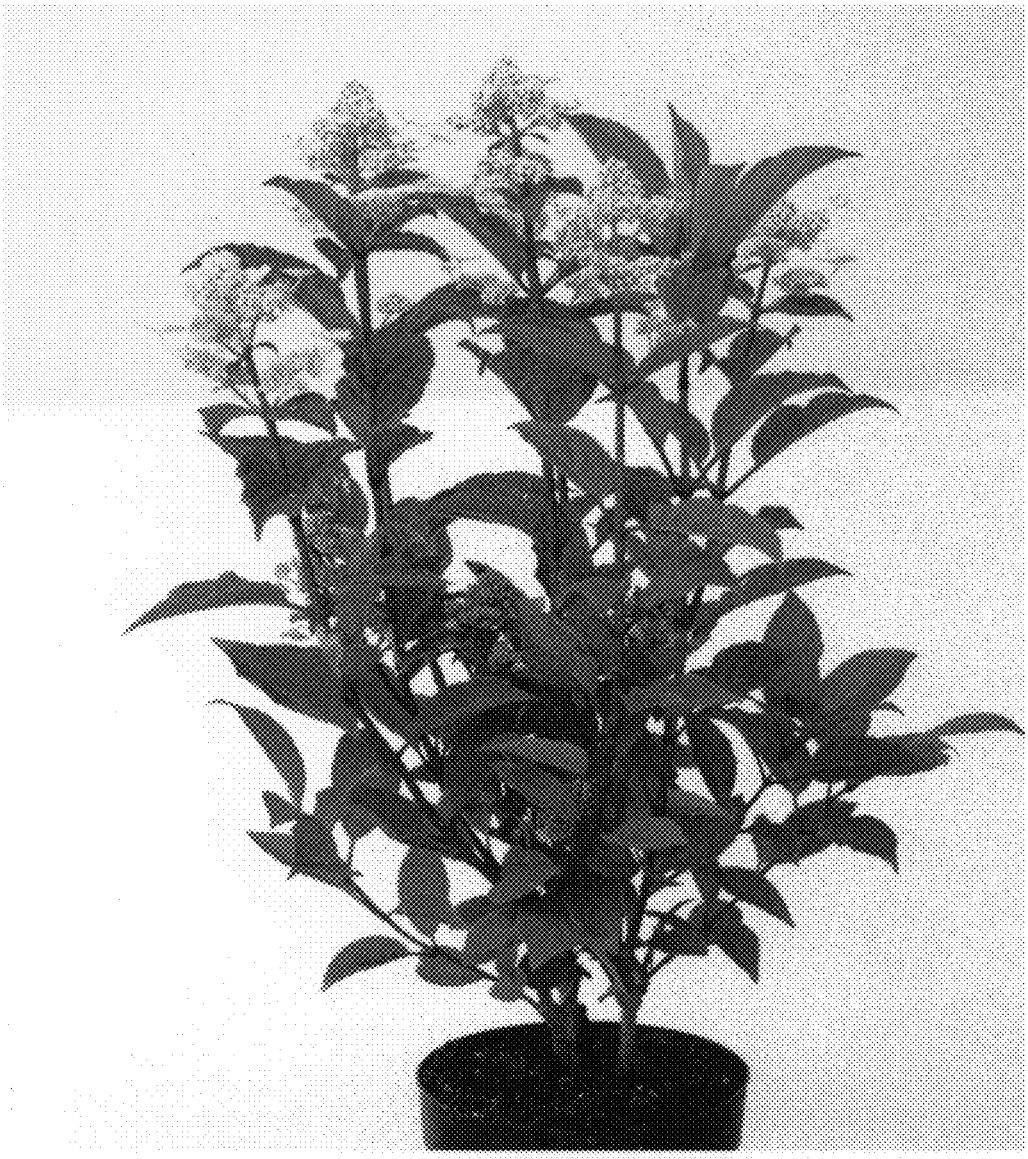
Figure 2:
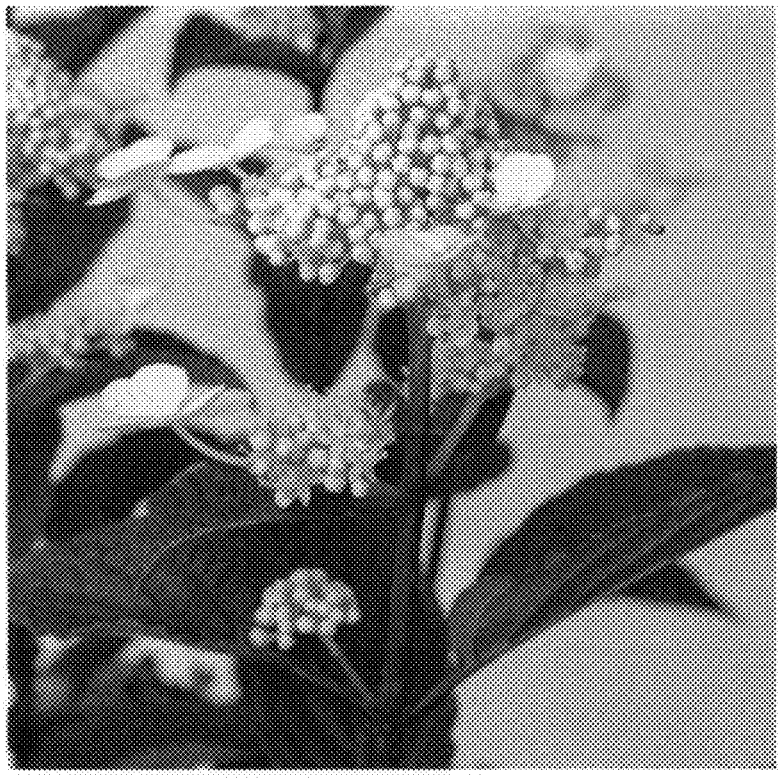

The photograph in FIG. 2 provides a close-up view of an inflorescence of 'HPOPR018'.

Figure 3:
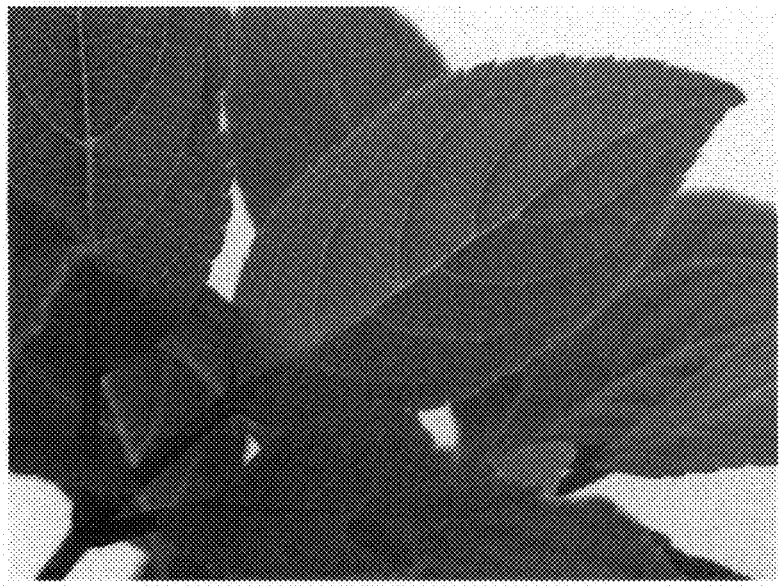

The photograph in FIG. 3 provides a close-up view of the foliage of 'HPOPR018'.

The colors in the photographs are as close as possible with the photographic and printing technology utilized and the color values cited in the detailed botanical description accurately describe the colors of the new *Hydrangea.*

BOTANICAL DESCRIPTION OF THE PLANT

The following is a detailed description of two-year-old plants of 'HPOPR018' as grown outdoors in 17-cm containers in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Approximately 5 weeks from early to late summer in The Netherlands.

*Plant type.*—Deciduous shrub, panicle type *Hydrangea.*

*Plant habit.*—Compact, upright to broadly upright.

*Height and spread.*—Reaches 56.3 cm in height and 46 cm in spread as grown in a 17-cm container, reaches about 1.5 m in height and spread as a mature plant in the landscape.

*Hardiness.*—At least in U.S.D.A. Zones 5 to 9.

*Diseases and pests.*—No susceptibility and resistance to diseases or pests has been observed.

*Root description.*—Fine, fibrous and dense, NN155A and 164A in color.

*Propagation.*—Softwood stem cuttings.

*Root development.*—An average of 30 days for root initiation with a young rooted plant produced in an average of 3 months.

*Growth rate and vigor.*—Moderate.

Stem description:

*Stem shape.*—Rounded.

*Stem strength.*—Strong.

*Stem color.*—Young; 184A, mature; 183B to 184A, bark N199A to N199B.

*Stem size.*—Average of 30.4 cm in length and 4 mm in diameter.

*Stem surface.*—Moderately covered with lenticels an average of 1.5 mm in length and 0.5 mm in diameter, color; on young and mature stems 185C to 185D, on older bark 165C, fascination absent.

*Stem aspect.*—Upright, average angle of 65° to soil level.

*Internode length.*—An average of 4.7 cm.

*Branching.*—Freely branching with an average of 16 lateral branches from the base.

Foliage description:

*Leaf shape.*—Ovate to narrowly ovate.

*Leaf arrangement.*—Opposite.

*Leaf division.*—Simple.

*Leaf base.*—Obtuse to short attenuate.

*Leaf apex.*—Apiculate.

*Leaf margins.*—Serrate.

*Leaf blade lobing.*—Absent.

*Leaf blade variegation.*—Absent.

*Leaf venation.*—Pinnate, color; color upper surface 153A, changing towards the petiole to 180B and 180A, lower surface 182A.

*Leaf size.*—An average of 8.9 cm in length and 4.6 cm in width.

*Leaf attachment.*—Petiolate.

*Leaf number.*—An average of 18 per lateral stem.

*Leaf surface.*—Both surfaces smooth, sparsely to moderately pubescent on main vein and secondary veins, upper side sparsely to moderately pubescent with very short adpressed strigose hairs; an average of 0.5 mm in length, color too small and too sparsely present to be measured, lower side main vein and secondary veins moderately pubescent with short adpressed hairs; average of 0.4 mm in length, color too small and too sparsely present to be measured.

*Leaf color.*—Young upper surface; a color between 137C and 143A, young lower surface; 138B and 191B, mature upper surface; 137A, mature lower surface; 138B.

*Petioles.*—An average of 2.1 cm in length and 3 mm in diameter, upper surface 185A in color and changing to 187A towards the proximal end, lower surface 185A in color and changing to 187B towards the proximal end, moderately glossy, glabrous, margins sparsely covered with very short hairs; average length 0.3 mm, color too small and too sparsely present to be measured.

Inflorescence description:

*Inflorescence type.*—Terminal conical compact panicle, comprised of single sterile flowers and fertile flowers, fertile flowers are clearly visible (very conspicuous).

*Lastingness of inflorescence.*—Sterile flowers; persistent for an average of 6 weeks, fertile flowers; self-cleaning, an average of 5 days.

*Inflorescence number.*—One per lateral stem.

*Inflorescence size.*—An average of 8.2 cm in height and 10 cm in diameter.

*Flower number.*—An average of 8 sterile flowers and 325 fertile flowers per panicle.

*Flower fragrance.*—Faint, sweet and pleasant.

*Flower aspect.*—Sterile flowers; upright, drooping when fading, fertile flowers; held upright from peduncle.

*Flower size.*—Sterile flowers; up to 2.8 cm in diameter and 6 mm in depth, fertile flowers; an average of 1 cm in diameter and 6.5 mm in depth.

*Flower type.*—Sterile flowers rotate, fertile flowers rotate, petals drop when mature.

*Flower buds.*—Sterile flowers; an average of 3 mm in length and 1.5 cm in diameter, saucer-shaped, 150D in color with margins 52B to 52C, fertile flowers; an average of 4 mm in length and 2.5 mm in diameter, obovate in shape, NN155D in color, immature calyx 145C in color.

*Peduncles.*—Primary peduncles; strong, flattened oval in shape, an average of 2.5 cm in length and 3 mm in width, secondary peduncles 2 cm in length and 2 mm in width, 157D in color and tinged with 183D to 184C, surface moderately covered with a thin pubescence; average of 0.3 mm in length, color between 145D and 150D.

*Pedicels.*—Sterile flowers; moderate strength, an average of 1.6 cm in length and 1.25 mm in width, 157D in color, held in an average angle of 25°, surface is matte, moderately covered with thin pubescence; average of 0.4 mm in length, 157D in color, fertile flowers; moderate strength, an average of 2 mm in length, 0.5 mm in diameter, held in an average angle of 30°, color between 145D and 150D, surface is matte, sparsely to moderately covered with a thin pubescence; average of 0.3 mm in length, color between 145D and 150D.

*Petals.*—Sterile flowers; average of 4, rotate, ovate to concave in shape, acute apex, cuneate base, entire margins, 3.5 mm in length, 2 mm in width, both surfaces glabrous, slightly glossy, matte, color when opening and fully open upper surface 155C, color when opening and fully open lower surface 155B, fertile flowers; average of 5, rotate, ovate to concave in shape, acute apex, cuneate base, entire margins, 3.5 mm in length and 2 mm in width, upper surface is glabrous and slightly glossy, lower surface glabrous and matte, color when opening and fully open upper surface 155C, color when opening and fully open lower surface 155B.

*Sepals.*—Sterile flowers; 4 (occasionally 3), rotate, broadly obovate in shape, apex is un-deeply emarginate to obtuse, base is broadly cuneate to truncate, entire margins, 1.4 cm in length, 1.3 cm in width, both surfaces glabrous and matte, color; when opening upper surface 150D, thin margins 52B to 52C, when opening lower surface 150D, margins 52C, when fully open upper surface 155A, thin margins 49A, when fully open lower surface NN155A, thin margins 49A, changing to 145B, fertile flowers; average of 5, rotate, deltoid in shape, broadly acuminate apex, broadly cuneate base, entire margins, 1 mm in length and width, both surfaces glabrous and matte, color; when opening and fully opening upper surface 145D, when opening lower surface 145C, when fully open lower surface 145D with tip 185D.

Reproductive organs:

*Gynoecium.*—Sterile flowers; not present, fertile flowers; 3 pistils, an average of 1.5 mm in length, stigma; club-shaped and 155C in color, style; 0.75 mm in length, 157D in color, ovary is 151C in color.

*Androecium.*—Sterile flowers; an average of 10 stamens, filaments; an average of 3 mm in length and 155C in color, anthers; broad oblong in shape, an average of 0.5 mm in length and 158D in color, pollen; low in quantity and 156D in color, fertile flowers; an average of 10 stamens, filaments; an average of 4 mm in length and NN155A in color, anthers; broad oblong in shape, an average of 0.5 mm in length and 158D in color, pollen; low in quantity and 156D in color.

*Fruit and seed.*—None observed to date.

It is claimed:

1. A new and distinct cultivar of *Hydrangea* plant named 'HPOPR018' substantially as herein illustrated and described.

* * * * *